US006176140B1

(12) United States Patent
Autenrieth et al.

(10) Patent No.: US 6,176,140 B1
(45) Date of Patent: Jan. 23, 2001

(54) METHOD OF TESTING CERAMIC COTYLOID CAVITIES FOR HIP JOINT ENDOPROSTHESES

(75) Inventors: Ralph Autenrieth, Esslingen; Hans-Georg Pfaff, Ostfildern; Herbert Richter, Kongen; Gerd Willmann, Leinfelden-Echterdingen; Martin Wimmer, Fellbach; Christian Worne, Stuttgart, all of (DE)

(73) Assignee: Cerasiv GmbH Innovatives Keramik-Engineering, Plochingen (DE)

( * ) Notice: Under 35 U.S.C. 154(b), the term of this patent shall be extended for 0 days.

(21) Appl. No.: 09/214,380
(22) PCT Filed: Jun. 26, 1997
(86) PCT No.: PCT/EP97/03351
  § 371 Date: Sep. 2, 1999
  § 102(e) Date: Sep. 2, 1999
(87) PCT Pub. No.: WO98/01090
  PCT Pub. Date: Jan. 15, 1998

(30) Foreign Application Priority Data
  Jul. 6, 1996 (DE) ............................................. 196 27 356
  Dec. 19, 1996 (DE) ............................................. 196 52 997
  May 2, 1997 (DE) ............................................. 197 18 615

(51) Int. Cl.[7] ...................................................... G01N 3/08
(52) U.S. Cl. ............................................... 73/824; 623/22
(58) Field of Search ........................... 73/818, 823, 824, 73/825, 856, 379.08; 623/22

(56) References Cited

U.S. PATENT DOCUMENTS

| | | | |
|---|---|---|---|
| 4,187,033 | * | 2/1980 | Zukowski ............................. 403/137 |
| 4,722,631 | * | 2/1988 | Tagami ................................. 403/133 |
| 4,840,631 | * | 6/1989 | Mathys .................................. 623/22 |
| 4,840,632 | * | 6/1989 | Kampner .............................. 623/22 |
| 4,966,108 | * | 10/1990 | Bentz et al. ........................ 123/90.51 |
| 5,649,779 | * | 7/1997 | Martin et al. .......................... 403/51 |

* cited by examiner

*Primary Examiner*—Max Noori
(74) *Attorney, Agent, or Firm*—Antonelli, Terry, Stout & Kraus, LLP

(57) ABSTRACT

A ceramic socket or ceramic socket insert for a hip joint prosthesis is tested prior to implantation in a human body by subjecting the portions of the interior of the socket or socket insert to a load that generates stresses that are greater than the physiological load. This may be accomplished either by pressing a hemispherically-shaped deformable material such as polymer or plastic into the interior of the socket or socket insert or by exposing the interior of the socket or socket insert to a fluid under pressure. The interior of the socket or socket insert may be sealed off with a test punch that has a supply line for the fluid. To reduce the amount of fluid that is required, the test punch may have a bulge that projects into the interior of the socket or socket insert and leaves only a gap for the fluid. In the method of testing, the interior of the socket or socket insert is subjected to a load that generates stress such that a defective socket or socket insert is destroyed and a non-defective socket or socket insert survives unharmed.

10 Claims, 2 Drawing Sheets

METHOD OF TESTING CERAMIC COTYLOID CAVITIES FOR HIP JOINT ENDOPROSTHESES

Figure 1:
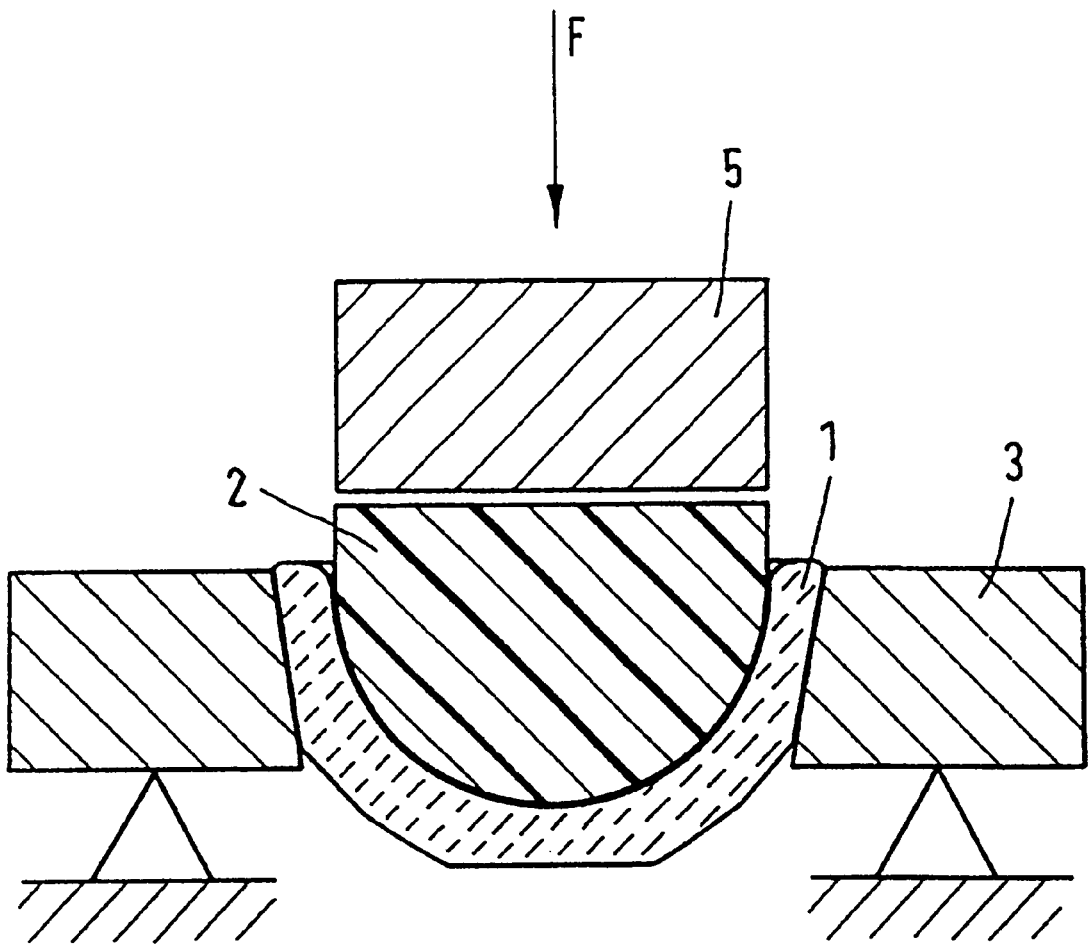

The invention relates to a method for testing ceramic sockets for hip joint endoprostheses according to the preamble of claim 1.

Systems with a modular design are normally used today for artificial hip joints, in other words a ball head is placed on a metal shaft with a pin, said head generally articulating with a socket made of polyethylene. The unavoidable abrasion, especially of the polyethylene, causes osteolysis that results in a loosening of the prosthesis and hence a repair operation.

This situation can be improved considerably if ceramic ball heads are used instead of metal ball heads. This is best accomplished by allowing ball heads made of aluminum oxide ceramic to articulate with socket inserts made of aluminum oxide ceramic.

Components of implants intended to be used in human beings must meet especially strict safety requirements. This also applies to ceramic components. Since ceramic materials are generally brittle, inhomogeneities in the material that concentrate stress lead especially easily to a fracture. This means that all parts containing defects that could result in fracture under application conditions must be detected and eliminated prior to use.

In quality control before now, only parts with defects on the surface could be eliminated by visual inspection. The known methods for non-destructive testing, such as x-ray fluoroscopy or ultrasonic testing, can theoretically be used for ceramic materials as well, but they are unable to detect defects of an extent that is small enough to be relevant for the required level of safety.

The primary goal of a final check however must be reliably to eliminate possibly defective parts in order to minimize any risk to the patient.

A requirement for the applicability and relevance of a proof test is that the load in the proof test must simulate as closely as possible the stress distribution that occurs in the part during use and also that no damage to the item being tested takes place as a result of handling while performing the proof test.

Thus for example a proof test in which the socket insert to be tested is inserted into an actual metal back is not possible, since it is not possible to remove the insert from the metal back after testing without damaging it.

A test would be possible in which the ceramic ball head is pressed into the ceramic socket or the ceramic socket insert with an overload (proof test). However, this test is not indicative since it merely results in a pointwise contact between the ball head and the ceramic socket insert, in other words not all of the contact areas between the ball head and socket can be adjusted during the test.

The goal of the invention is to provide a method for testing ceramic socket inserts that provides assurance that any defective socket inserts will be detected and eliminated during the quality check without there being any danger of damaging the socket inserts.

This goal is achieved according to the invention by the following:

All of the volume elements of the socket that are under load in the physiological load case are loaded;

Stresses are generated in the socket or in the socket insert that are higher by a specific factor than the stresses that are developed in the physiological load case.

Hence, the invention relates to a proof test device or method in which the ceramic socket inserts can be subjected to the necessary specific overload and in which the sockets can be removed from the device without damage.

The advantage of this method is that all of the ceramic sockets in which there are critical defects in the volume or on the surface will fail under load. Hence, this method is not only a test that discovers defective parts but also destroys all the defective parts.

The stress distribution in ceramic sockets is known from the results of a calculation of stress using the finite element method.

The ceramic sockets or socket inserts preferably consist of high-strength biocompatible ceramic, so-called bioceramic. In particular, these are aluminum oxide ceramic (medical-grade aluminia), zirconium oxide ceramic of the Y-TZP type, materials based on zirconium oxide/aluminum oxide, non-oxide ceramics such as silicon nitride, silicon carbide, and silicon aluminum nitride.

A preferred version is characterized by the fact that a hemisphere made of a deformable material is pressed under load into the socket.

Advantageously, the deformable material of the hemisphere is a polymer or a plastic.

In an alternative, especially preferred version, the interior of the socket is loaded by a fluid under pressure. This can produce fracture patterns that match those from bursting tests with hip joint balls. It can then be assumed that loading by a fluid pressure closely simulates the loading in a burst test.

Advantageously, a test punch is placed on the socket which seals off the interior of the socket from the outside by a sealing element and has a supply line for the fluid.

To reduce the fluid volume required, the test punch advantageously projects by a bulge into the socket and leaves only a gap for the fluid.

Logically, the socket to be tested is placed in a holder, so that according to the invention the holder supports the socket only at its conical upper end by means of a sealing element. The socket is anchored in the metal shell of the hip joint endoprosthesis by this conical part.

According to the invention, the fluid is a fluid suitable for high pressure, for example water or glycerin.

Further features of the invention will be found in the figures described below.

FIG. 1 shows an embodiment of the testing device according to the method according to the invention. A ceramic socket 1 for a hip joint endoprosthesis is inserted into a holder 3 in such fashion that it can be easily removed again after the test. The lower half of socket 1 projects from holder 3. Holder 3 in this case is in the form of a plate. For testing, a hemisphere 2 made of a deformable material is inserted into socket 1 and subjected to a load by a punch 5, said load being a multiple of the maximum physiological load case. In order for all the volume elements of socket 1 that are under load in the physiological load case to be loaded, hemisphere 2 fills socket 1 completely. If there is a defect in the volume or on the surface of socket 1, the latter will break. Therefore, all defective sockets 1 are destroyed.

The deformable material of hemisphere 2 advantageously consists of a polymer plastic, for example polytetrafluoroethylene, polyurethane or silicone rubber, or Teflon.

Figure 2:
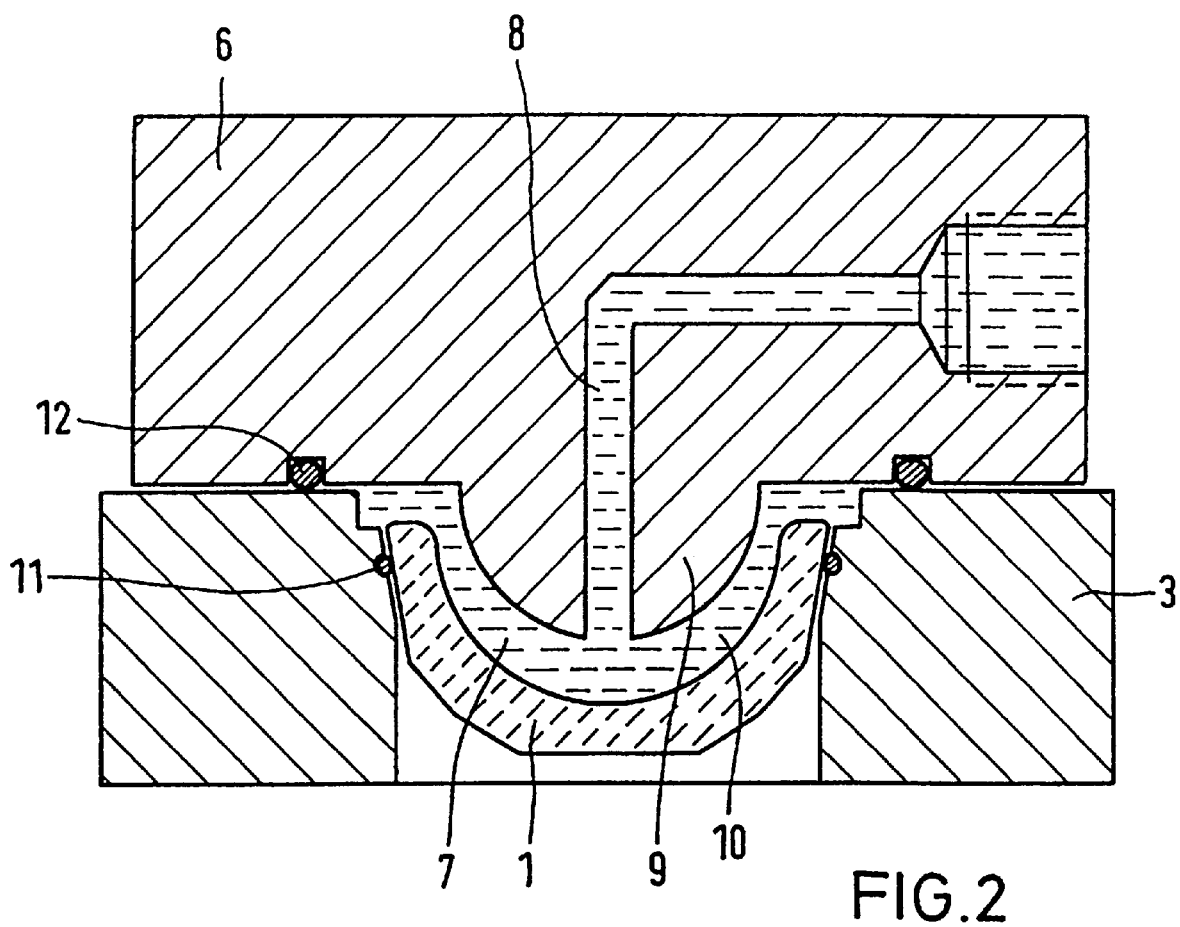

FIG. 2 shows a preferred embodiment in which the interior of socket 1 is loaded by a fluid 7 under pressure. Socket 1 to be tested is inserted into a holder 3 with a sealing element 11, with sealing element 11 supporting the socket preferably only at its conical upper end. A test punch 6 is placed on holder 3 with socket 1 inserted, said punch in a preferred embodiment having a bulge 9 by which it projects into socket 1, so that only a gap 10 remains between test punch 6 and its bulge 9 and the interior of the socket. A sealing element 12 is located between test punch 6 and holder 3 and seals off the internal volume of socket 1 from the outside.

A supply line 8 is provided in test punch 6 and bulge 9, through which line the fluid can be admitted under pressure into gap 10.

When testing socket 1, the latter is placed in holder 3 and test punch 6 is applied. Then fluid is supplied under pressure through supply line 8, creating a stress in the socket which is higher by a specific factor than the stress developed in the physiological load case. Sockets with defects considered to be critical will be destroyed during this test. Those sockets that survive the test have a strength that is higher than the limit defined by the overload test.

What is claimed is:

1. A method for testing a ceramic socket or a ceramic socket insert for a hip joint endoprostheses, the ceramic socket or ceramic socket insert having an interior and being of a type wherein upon implantation in a human body, the ceramic socket or ceramic socket insert is anchored to a pelvic bone, either directly or by an outer shell and wherein a ceramic ball head is inserted into the ceramic socket or ceramic socket insert, the ceramic ball being mounted onto a metal shaft that is anchored in a thigh bone with a pin and wherein during usage of a ceramic socket or ceramic socket insert after implantation of the ceramic socket or ceramic socket insert in a human body, portions of the ceramic socket or ceramic socket insert that define an interior of the ceramic socket or ceramic socket insert are placed under a physiological load, the method of testing being carried out prior to implantation of the ceramic socket or ceramic socket insert in a human body, wherein the method of testing comprises the step of:

subjecting the interior of the ceramic socket or ceramic socket insert to a load, wherein the load generates stresses in the interior of the ceramic socket or ceramic socket insert on all portions of the ceramic socket or ceramic socket insert that would be placed under a physiological load during usage after implantation of the ceramic socket or ceramic socket insert in a human body and wherein the magnitude of the stresses that are generated by the load are greater that the magnitude of the stresses that would be placed on the portions of the ceramic socket or ceramic socket insert under a physiological load during usage after implantation of the ceramic socket or ceramic socket insert in a human body.

2. The method of claim 1, wherein the step of subjecting the interior of the ceramic socket or ceramic socket insert to a load is carried out by pressing a hemispherically-shaped deformable material into the interior of the ceramic socket or ceramic socket insert.

3. The method of claim 2 wherein the deformable material is made of a polymer or plastic.

4. The method of claim 1 wherein the step of subjecting the interior of the ceramic socket or ceramic socket insert to a load is carried out by a step of exposing the interior of the ceramic socket or ceramic socket insert to a fluid that is under pressure.

5. The method of claim 4 wherein the step of exposing the interior of the ceramic socket or ceramic socket insert to a fluid under pressure is carried out by providing a test punch, placing the test punch on the ceramic socket or ceramic socket insert so that the interior of the ceramic socket or ceramic socket insert is sealed off, providing a supply line for supplying fluid into the interior of the ceramic socket or ceramic socket insert, and supplying a fluid under pressure into the interior of the ceramic socket or ceramic socket insert.

6. The method of claim 5 wherein the test punch has a bulge shape such that when the test punch is placed on the ceramic socket or ceramic socket insert, the test punch projects into the interior of the ceramic socket or ceramic socket insert so that the test punch occupies a volume of the interior of the ceramic socket or ceramic socket insert and so that a gap is defined between the test punch and the portions of the ceramic socket or ceramic socket insert that define the interior of the ceramic socket or ceramic socket insert and wherein in the step of supplying a fluid under pressure into the interior of the ceramic socket or ceramic socket insert, the fluid is supplied into the gap between the test punch and the portions of the ceramic socket or ceramic socket insert that define the interior of the ceramic socket or ceramic socket insert.

7. The method of claim 1 wherein before the interior of the ceramic socket or ceramic socket insert is subjected to a load, the ceramic socket or ceramic socket insert is placed in a holder.

8. The method of claim 7 wherein the ceramic socket or ceramic socket insert has an exterior portion having a lower end defining a base of the ceramic socket or ceramic socket insert and an upper end defining an opening surrounding the portions that define the interior of the ceramic socket or ceramic socket insert, wherein the exterior portion tapers outwardly from the lower end to the upper end, wherein the holder includes a sealing element and wherein when the ceramic socket or ceramic socket insert is placed in the holder, the only contact between the holder and the ceramic socket or ceramic socket insert is between the sealing element and the upper end of the exterior portion of the ceramic socket or ceramic socket insert.

9. The method of claim 4 wherein the fluid is a fluid that is capable of imparting a high pressure.

10. The method of claims 4 wherein the fluid is water or glycerin.

* * * * *